US006765984B2

(12) United States Patent
Higgins et al.

(10) Patent No.: US 6,765,984 B2
(45) Date of Patent: Jul. 20, 2004

(54) DEVICE FOR CUSHIONING OF COMPRESSION SURFACES

(75) Inventors: Sheryl W. Higgins, Silvarado, CA (US); George D. Hermann, Portola, CA (US); David Willis, Palo Alto, CA (US); Thomas A. Howell, Palo Alto, CA (US); Gail Lebovic, Palo Alto, CA (US)

(73) Assignee: Biolucent, Inc., Aliso Viejo, CA (US)

( * ) Notice: Subject to any disclaimer, the term of this patent is extended or adjusted under 35 U.S.C. 154(b) by 217 days.

(21) Appl. No.: 09/922,602

(22) Filed: Aug. 3, 2001

(65) Prior Publication Data

US 2003/0007597 A1 Jan. 9, 2003

Related U.S. Application Data

(63) Continuation-in-part of application No. 09/620,730, filed on Jul. 20, 2000, now Pat. No. 6,577,702.
(60) Provisional application No. 60/187,198, filed on Mar. 6, 2000.

(51) Int. Cl.$^7$ .................................................. A61B 6/04
(52) U.S. Cl. ......................................... 378/37; 378/208
(58) Field of Search .............................. 378/37, 62, 68, 378/208

(56) References Cited

U.S. PATENT DOCUMENTS

| | | | |
|---|---|---|---|
| 3,963,933 A | | 6/1976 | Henkes, Jr. |
| 4,259,585 A | * | 3/1981 | Novak et al. ................. 378/37 |
| 4,346,298 A | | 8/1982 | Dixit |
| 4,433,690 A | | 2/1984 | Green et al. |
| 4,691,333 A | | 9/1987 | Gabriele et al. |
| 4,923,187 A | | 5/1990 | Monbrinie |
| 4,943,986 A | | 7/1990 | Barbarisi |
| 5,044,008 A | | 8/1991 | Jackson |

(List continued on next page.)

FOREIGN PATENT DOCUMENTS

| | | |
|---|---|---|
| DE | 23 35 576 A1 | 1/1975 |
| DE | 4324508 A1 | 1/1995 |
| DE | 199 26 446 A1 | 1/2000 |
| DE | 199 21 100 A1 | 3/2000 |
| EP | 0 682 913 A1 | 11/1995 |
| FR | 2 702 059 | 9/1994 |
| FR | 2 702 059 A1 | 9/1994 |
| GB | 938410 | 6/1962 |
| WO | WO 96/07353 | 3/1996 |
| WO | WO 01/66013 A2 | 9/2001 |

OTHER PUBLICATIONS

PCT Publication No. WO 96/13211, "Apparatus and Method for Improved Tissue Imaging", May 9, 1996.
43$^{rd}$ Annual Meeting of the American Association of Physicists in Medicine, Jul. 22–26, 2001, Salt Lake City, Utah, "The Breast Pillow™: A Novel Device to Reduce Patient Discomfort and Pain During Mammography While Also Measuring Compression Force"., http://www.aapm.org/mmeetings/01am/prabs.asp?mid=6&aid=7295, 2 pgs.
S&S Par Scientific, VacFix Literature, HP002/0307, Houston, TX.

*Primary Examiner*—Louis Arana
(74) *Attorney, Agent, or Firm*—William A. English; Cohen & Sakaguchi, LLP

(57) ABSTRACT

A pad for cushioning a compression device, e.g., an x-ray plate, of a mammography unit. The pad includes a radiolucent central region, e.g., including radiolucent orientation markings, that is secured adjacent a contact surface of the x-ray plate. The pad includes a pair of side regions secured along respective side surfaces of the x-ray plate including a slot for inserting an x-ray cassette into the x-ray plate. The pad also includes a front region securable along a front surface of the x-ray plate. A double coated tape may be attached to the pad that includes a pressure sensitive adhesive for removably attaching the pad to the x-ray plate. Alternatively, the side regions may extend around the compression device and connect to one another to secure the pad or the pad may be a sleeve that is slidably received around at least a portion of the compression device.

50 Claims, 10 Drawing Sheets

U.S. PATENT DOCUMENTS

| | | |
|---|---|---|
| 5,081,657 A | 1/1992 | Klawiter et al. |
| 5,161,273 A | 11/1992 | Deck |
| 5,166,968 A | 11/1992 | Morse |
| 5,185,776 A | 2/1993 | Townsend |
| 5,189,686 A | 2/1993 | Hixson, Sr. |
| 5,226,070 A | 7/1993 | Ariba et al. |
| 5,260,985 A * | 11/1993 | Mosby ........................ 378/164 |
| 5,377,254 A | 12/1994 | Walling |
| 5,398,272 A | 3/1995 | Bouscary et al. |
| 5,474,072 A | 12/1995 | Shmulewitz |
| 5,479,927 A | 1/1996 | Shmulewitz |
| 5,541,972 A | 7/1996 | Anthony |
| 5,553,111 A | 9/1996 | Moore et al. |
| 5,613,254 A | 3/1997 | Clayman |
| 5,632,275 A | 5/1997 | Browne et al. |
| 5,657,367 A | 8/1997 | Couch |
| 5,719,916 A | 2/1998 | Nelson et al. |
| 5,754,997 A | 5/1998 | Lussi et al. |
| 5,832,550 A | 11/1998 | Hauger et al. |
| 5,891,074 A | 4/1999 | Cesarczyk |
| 6,049,583 A | 4/2000 | Galkin |

\* cited by examiner

DEVICE FOR CUSHIONING OF COMPRESSION SURFACES

This application is a continuation-in-part of application Ser. No. 09/620,730, filed Jul. 20, 2000 now U.S. Pat. No. 6,577,702, which claims priority of provisional application Serial No. 60/187,198, filed Mar. 6, 2000, the disclosures of which are expressly incorporated herein by reference.

FIELD OF THE INVENTION

The present invention relates generally to devices and methods for cushioning surfaces, and more particularly to devices and methods for cushioning or padding surfaces of compression plates applied to body parts during x-ray procedures, for example, during mammography, biopsies, and the like.

BACKGROUND

During mammography, a patient's breast is placed under compression by opposing plates attached to a mammography unit. Once under compression, an x-ray may be taken to determine the presence or absence of suspect lesions in the breast tissue, e.g., calcifications or tumors. An important reason for compressing the breast during mammography is to provide a thinner cross-section of tissue for the x-rays to pass through. When the breast is compressed, it may provide optimal imaging of tissue abnormalities and/or may allow lower doses of x-ray radiation to be used, thereby reducing x-ray radiation exposure to the patient.

FIGS. 1, 2A, and 2B show a mammography unit 10, including a base 12 and a rotating assembly 14 that includes an x-ray source 16, a compression paddle 18, and an x-ray plate 20. The x-ray plate 20, often referred to as a "bucky," is stationary relative to the rotating assembly 14, while the compression paddle 18 may be attached to an interchange assembly 22 that is movable relative to the x-ray plate 20.

As best seen in FIG. 2A, the x-ray plate 20 generally includes two patient contact surfaces, a primary tissue contact surface 24 and a front surface 26, as well as side surfaces 28. At least one of the side surfaces 28 may include an opening 30 into which an x-ray cassette 32 may be inserted. FIGS. 4A and 4B show attachments that may be placed on the x-ray plate 20 to enhance imaging, e.g., an attachment 40 for spot compression and an attachment 42 for magnification.

As best seen in FIG. 2B, the compression paddle 18 also generally includes two patient contact surfaces, a primary tissue contact surface 34 and a front surface 36, as well as two side surfaces 38. FIGS. 3A–3C show other configurations of compression paddles 44–48 that may have various shapes and sizes depending upon a patient's anatomy and/or the type of x-ray view that is desired.

With the patient (not shown) leaning against the front surfaces 26, 36, the patient's breast (also not shown) is placed on the primary contact surface 24 of the x-ray plate 20 and the compression paddle 18 is moved towards the x-ray plate 20 to compress the breast between the primary contact surfaces 24, 34. A series of x-rays may be taken of the breast tissue, e.g., involving moving the rotating assembly 14 and/or repositioning the patient's breast after each film exposure.

One of the problems with mammography is that the patient may experience significant discomfort during compression of the breast. Because of this, some women may avoid having a mammogram taken, rather than experience the pain that may be caused during the procedure. Although patients may tolerate the pain caused by compression up to about ten to eleven (10–11) compression units, clinical mammography may involve up to sixteen to eighteen (16–18) compression units. If greater compression is used, the quality of the mammogram may be enhanced, thereby increasing the physician's ability to detect cancers or suspect lesions. However, with greater compression comes increased discomfort.

U.S. Pat. No. 5,541,972, issued to Anthony, discloses a padding device that may be added to cover the front surface of an x-ray plate. Because the padding device is made from materials that may be radiopaque, the padding device is generally positioned to avoid disposing it within the field of the x-ray plate.

U.S. Pat. No. 5,185,776 discloses a radiolucent pad that is glued to a sleeve. An x-ray cassette may be inserted into the sleeve, a patient may be disposed against the pad, and an x-ray image obtained. The sleeve and pad are disposed of after the x-ray procedure. Disposing of the entire x-ray sleeve after a single use, however, may increase the cost of x-ray procedures.

Accordingly, improved devices and methods for increasing patient comfort during mammography and/or for allowing increased compression without substantially increased discomfort would be useful.

SUMMARY OF THE INVENTION

The present invention is directed to devices and methods for cushioning surfaces, for example, for cushioning or padding surfaces of compression devices applied to body parts during x-ray procedures, such as during mammography, biopsies, and the like.

In accordance with one aspect of the present invention, a compressible and/or resilient pad is provided for cushioning a compression surface of a mammography unit. The pad is formed at least partially from radiolucent material, and includes first and second surfaces. A radiolucent tape includes a first surface that is attached to the first surface of the pad, and a second exposed surface that includes a radiolucent pressure sensitive adhesive for removably attaching the exposed surface to an object.

Preferably, the tape is a double coated tape, e.g., including a polyester or polyethylene base film, and an acrylic adhesive on the first and second surfaces. The adhesive on the first surface may substantially permanently attach the tape to the first surface of the pad, while the adhesive on the exposed surface may allow attachment to an object, such as an x-ray plate, a compression paddle, or other compression device. A cover sheet may cover the exposed surface of the tape, the cover sheet being removable before attaching the exposed surface to an object.

In one embodiment, the entire pad may be formed from radiolucent material, while alternatively, the pad may include a radiolucent region, e.g., a central region, and a radiopaque region, e.g., a border around the central region. The pad may include one or more side regions adjacent the central region, at least one of which may include a slot therethrough. In a further alternative, the pad may include a window for providing access through the pad.

In accordance with another aspect of the present invention, an apparatus is provided for compressing a tissue structure using a compression device that includes a primary contact surface formed from radiolucent material, and one or more side surfaces extending laterally from the primary contact surface. The compression device may be an x-ray plate, a compression paddle, or an attachment to such devices. A pad, such as that described above, may be secured to the compression device. The pad includes a tissue contact surface formed from radiolucent material that may be removably secured against the primary contact surface, and one or more side regions removably secured along respective side surfaces of the compression device. In one embodiment, the pad may include a pair of side regions extending from opposing edges of the tissue contact surface. The side regions may extend around the compression device and connect to one another such that the tissue contact surface is secured adjacent the primary contact surface of the compression device with or without using an adhesive. In addition, or alternatively, the pad may include a front region removably secured to a front surface of the compression device. The front region may simply cover the front surface or it may be sufficiently long such that the front region and at least one of the side regions overlap to substantially secure the pad to the compression device.

In another embodiment, the pad may be a sleeve that may be received around at least a portion of the compression device. Preferably, the pad is sized to slidably engage the compression device sufficiently to secure the tissue contact surface adjacent the primary contact surface. The sleeve may include a top panel, side panels, a bottom panel, and/or a back panel. One or more side regions may include a slot therein corresponding to an opening in a side surface of the compression device, thereby providing access to the opening when the side region is secured adjacent the side surface, e.g., to insert an x-ray cassette into the compression device.

In accordance with yet another aspect of the present invention, a device is provided for attachment to a compression device of a mammography unit or a stereotactic biopsy unit. The device generally includes a pad formed at least partially from radiolucent material. The pad includes first and second surfaces, and markings for orienting a tissue structure applied against the second surface. The markings may include notches or indents in at least one of the first and second surfaces and/or in one or more edges of the pad. The markings may be radiolucent (i.e., detectable visually, but undetectable by x-ray). Alternatively, the markings may be radiopaque, e.g., printed on at least one of the first and second surfaces.

In addition, the device may include a layer of adhesive for removably attaching the first surface of the pad to the compression device. For example, a radiolucent adhesive may be applied directly to the first surface, such as a pressure sensitive adhesive. Alternatively, the first surface may include a texture, e.g., an inherent texture of the first surface or a texture applied to the first surface, to provide sufficient friction between the first surface and an object.

Preferably, the layer of adhesive includes a double coated tape attached to the first surface, as described above. Polyethylene tape may be preferred because of its elasticity, which may facilitate securing the device around corners of a compression device while minimizing creation of air pockets or creases that may be visible on an x-ray image. The device may be attached to a compression device and/or may include other features, e.g., similar to the embodiments described above.

Other objects and features of the present invention will become apparent from consideration of the following description taken in conjunction with the accompanying drawings.

BRIEF DESCRIPTION OF THE DRAWINGS

FIG. 14 is a top view of a "U" shaped pad for use with a stereotactic biopsy apparatus.

DETAILED DESCRIPTION OF THE PREFERRED EMBODIMENTS

Figure 5:
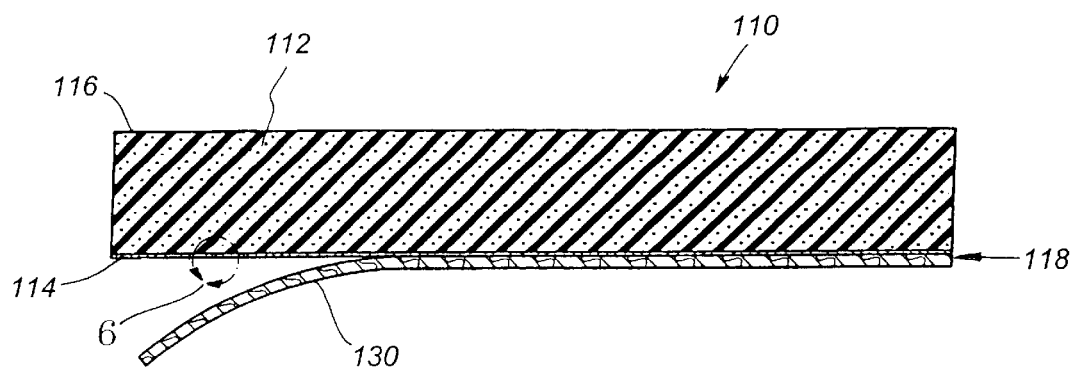
FIG. 5 is a cross-sectional view of a pad, in accordance with the present invention.
Figure 6:
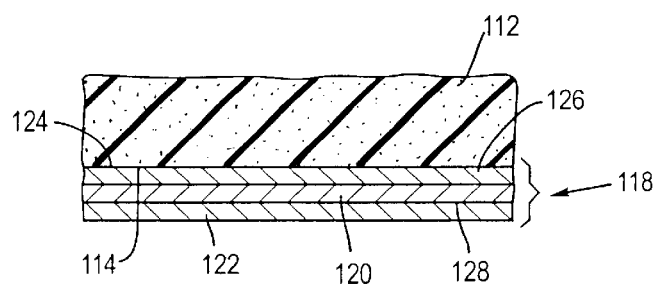
FIG. 6 is a cross-sectional detail of an adhesive layer of the pad of FIG. 5.

Turning now to the drawings, FIGS. 5 and 6 show a cross-section of a preferred embodiment of a pad 110, in accordance with the present invention. Generally, the pad 110 includes a padding layer 112 of compressible and/or resilient material defining first and second surfaces 114, 116, and a layer of adhesive 118 attached to the first surface 114.

The padding layer 112 may be constructed from one or more materials in a configuration that produces no significant visual artifacts on a mammogram (i.e., are radiolucent), and/or that are resiliently deformable under forces applied during compression to provide comfort. In addition, it may be desirable for the materials to conform to one or more surfaces of a compression device, e.g., an x-ray plate or a compression paddle, such as those shown in FIGS. 2A–4C, and/or directly to tissue. This conformability may minimize the risk of air pockets and/or folds that may be visible on an x-ray image. Further, it may be desirable for the materials to absorb external fluids, such as sweat. In addition, it may be desirable that the materials be thermally insulating.

Preferably, the padding layer 112 is formed from a single sheet of elastomer or gel, e.g., an open cell foam, such as polyolefin or polyurethane. More preferably, the padding layer 112 is a sheet of polyurethane open cell foam, such as a five or six pound (5–6 lb.) density foam, that has excellent radiolucent characteristics and a substantially soft tactile feel. In exemplary embodiments, the padding layer 112 may have a thickness of between about 1.27 millimeters (0.050 inch) and 12.7 millimeters (0.500 inch), and preferably between about 5.08 millimeters (0.200 inch) and 6.35 millimeters (0.250 inch).

Figure 12A:
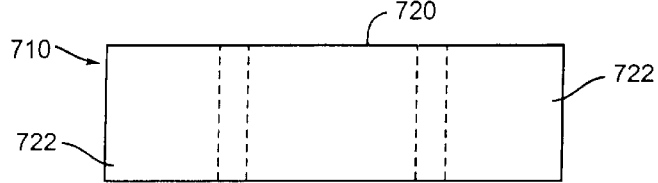
FIGS. 12A–12D are top views of wrap-around pads that may secured around a compression device, as shown in FIG. 11.

In an alternative embodiment, shown in FIG. 12A and described further below, the padding layer may include one or more regions that are substantially radiolucent and one or more additional regions that are not radiolucent and/or are radiopaque. For example, the exemplary pad 710' shown in FIG. 12A includes a central radiolucent window 721' and a perimeter 720' that is radiopaque.

Turning to FIG. 6, the layer of adhesive 118 is preferably a double coated tape 120 that includes first and second surfaces 122, 124 coated with adhesives 126, 128. For example, the tape 120 may include a polyester or polyethylene film. Polyethylene may be more elastic, i.e., flexible and/or stretchable than polyester, and therefore may be preferred if the pad 110 is being stretched and/or bent along surfaces, as described further below. The tape 120 may have a thickness of between about one and ten (1–10) mils, and preferably not more than about 3 mils.

Preferably, the adhesives 126, 128 are pressure sensitive, such as an acrylic or synthetic rubber adhesive. The adhesive 126 on the first surface 122 may substantially permanently attach the tape 120 to the padding layer 112. The adhesive 128 on the second surface 124 may have sufficient tackiness to securely, but detachably, attach the pad 110 to a surface, e.g., of a compression device or tissue (not shown). Preferably, the adhesive 128 allows easy removal of the pad 110 from the surface, e.g., leaving substantially no residue of adhesive on the surface. The adhesive 126 on the first surface 122 may have a thickness of between about one and five (1–5) mils, and preferably not more than about 1.25 mils. The adhesive 128 on the second surface 124 may have a thickness of between about one and five mils, and preferably not more than about 1.25 mil.

In an alternative embodiment, a pressure sensitive adhesive (not shown) may be applied directly to the first surface 114 of the padding layer 112. In a further alternative, a non-adhesive gel may be applied to the first surface 114 and/or to the compression surface (not shown) that provides a sufficient coefficient of friction between the pad 110 and the compression surface to secure the pad 110 in place. In yet a further alternative, the first surface 114 of the padding layer 112 may include a texture (not shown) such that the first surface is sufficiently tacky to allow removable attachment of the pad to a surface, e.g., by friction with or without the need for an adhesive. For example, the inherent texture of the foam defining the padding layer 112 may be sufficiently skid-free for use on a top surface of a device, such as an x-ray plate. Alternatively, additional texturing may be created in the first surface 114 to enhance frictional engagement with a contact surface. In a further alternative, a material (not shown) may be applied to the first surface 114 to provide a desired texture.

In a preferred embodiment, the layer of adhesive 118 may cover the entire first surface 114, and therefore the layer of adhesive 118 should be radiolucent. Alternatively, the layer of adhesive 118 may cover one or more particular regions of the first surface 114, e.g., along the outer border (not shown). In this alternative embodiment, the layer of adhesive 118 may be radiopaque in one or more regions that are outside the field of an x-ray plate and radiolucent if inside the field of the x-ray plate.

Optionally, as shown in FIG. 5, a peel-away cover sheet 130 may be provided over the layer of adhesive 118. Alternatively, a peel-away packet (not shown) may be provided within which the pad 110 may be stored before use.

Figure 7A:
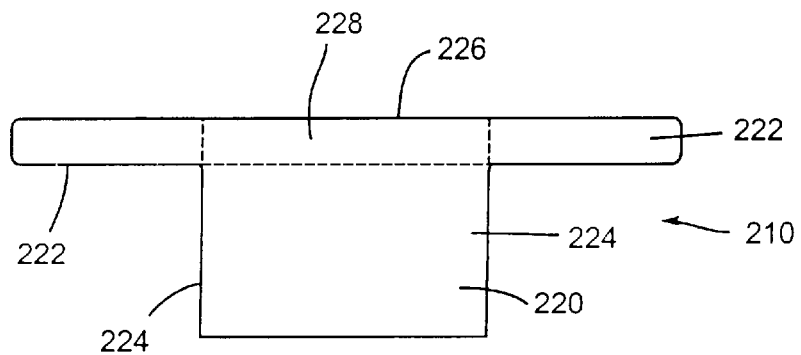
FIGS. 7A–7C are top views of various embodiments of cushioning pads, in accordance with the present invention.
Figure 8:
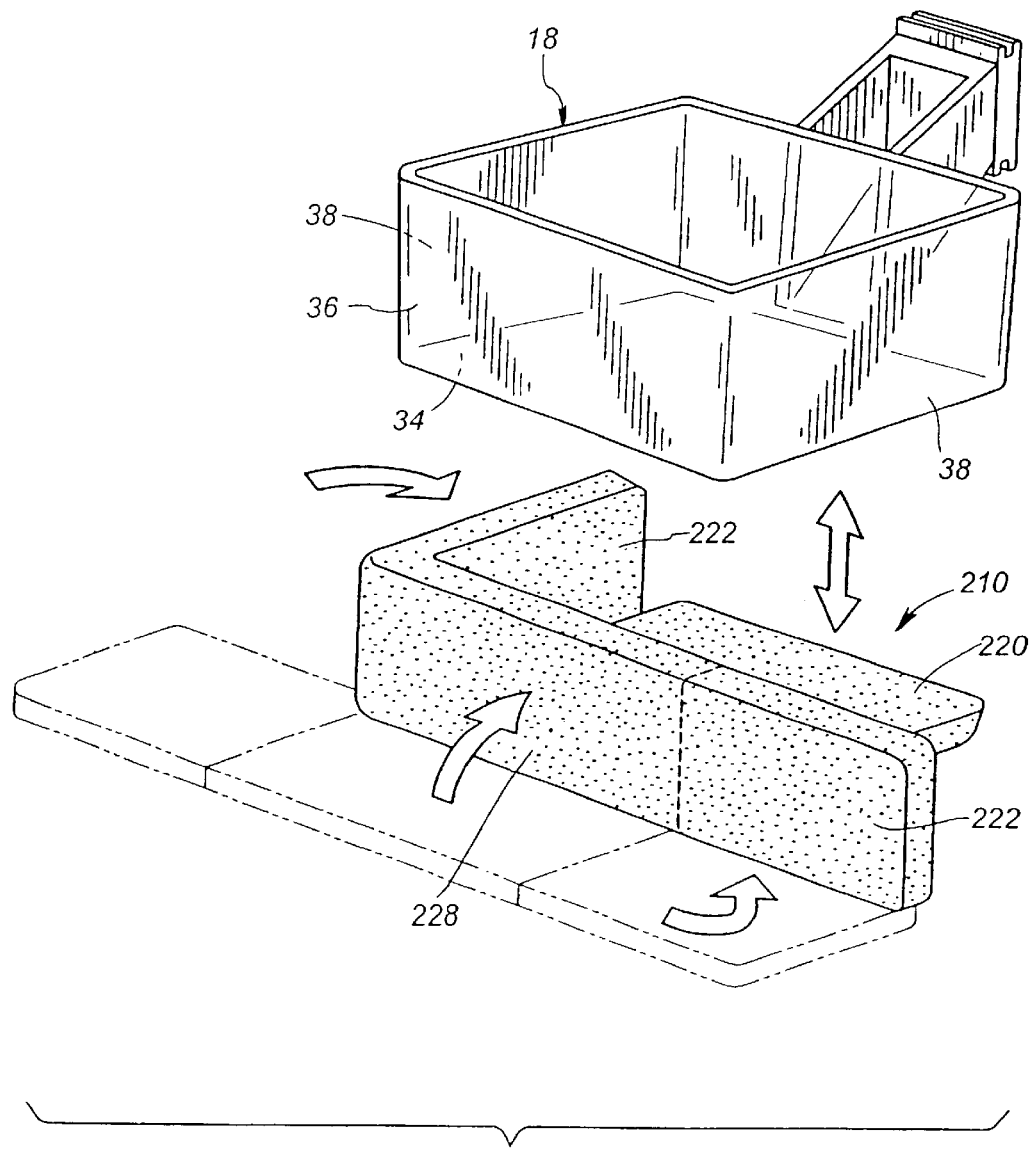
FIG. 8 is a perspective view of a compression paddle having the pad of FIG. 7A attached thereto.

Turning to FIGS. 7A and 8, a first preferred embodiment of a pad 210 is shown, having a generally "T" shape, including a central region 220 and a pair of wings 222 extending from opposing side edges 224 of the pad 210. Preferably, the wings 222 extend along a front edge 226 of the pad, thereby defining a front region 228 between the wings 222.

As best seen in FIG. 8, the pad 210 may be attached to primary contact, front, and side surfaces 34, 36, 38 of a compression paddle 18. The pad 210 may be placed with the second surface facing downward or away from the compression paddle 18. A cover sheet (if provided) may be removed from the layer of adhesive (not shown), and the central region 220 may be aligned with the primary contact surface 34 such that the front region 228 may be bent and applied to the front surface 36 of the compression paddle 18. The wings 222 may then be bent and applied along the side surfaces 38. Thus, the pad 210 may provide cushioning along the front and side surfaces 36, 38, as well as the primary contact surface 34, which may increase a patient's comfort, particularly if the patient's body is pressed against the front and side surfaces 36, 38, and/or the corners between them.

Figure 7B:
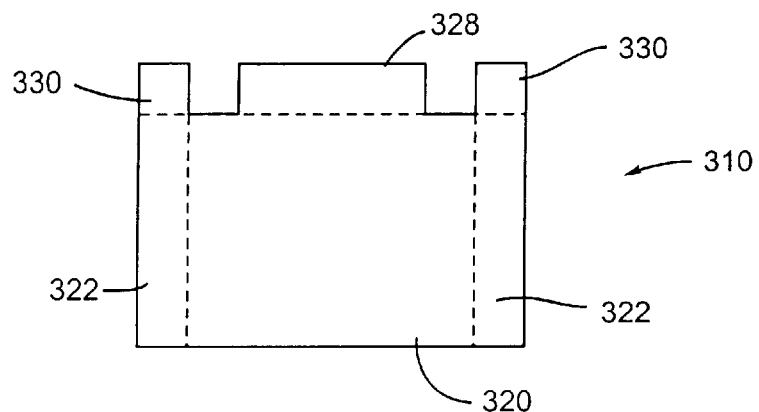

Turning to the FIG. 7B, an alternative embodiment of a pad 310 is shown that includes a central region 320, side regions 322 including ears 330, and a front region 328. Similar to the previous embodiment, the central region 320 may be aligned and applied to a primary contact surface 34 of a compression paddle 18 (not shown in FIG. 7B) such that the front region 328 may be bent and applied against the front surface 36. The side regions 322 may be bent and applied against the side surfaces 38, and then the ears 330 may be bent to cover the balance of the front surface 36. One advantage of this embodiment is that it may minimize waste of pad material as compared with cutting or otherwise forming the "T" shaped pad 220 of FIG. 7A.

In a further alternative, shown in 7C, a pad 410 may be provided that includes front and side regions 428, 422 extending from a central region 420. The front and side regions 428, 422 may be applied against front and side surfaces 36, 38 of a compression paddle 18 when the central region 420 is applied against a primary contact surface 34. For the embodiments shown in FIGS. 7A–7C, it may be preferable to use a polyethylene double coated tape (not shown) in the layer of adhesive. A polyethylene film may stretch and/or otherwise conform better when bent around corners of the compression paddle than a polyester film.

Figure 1:
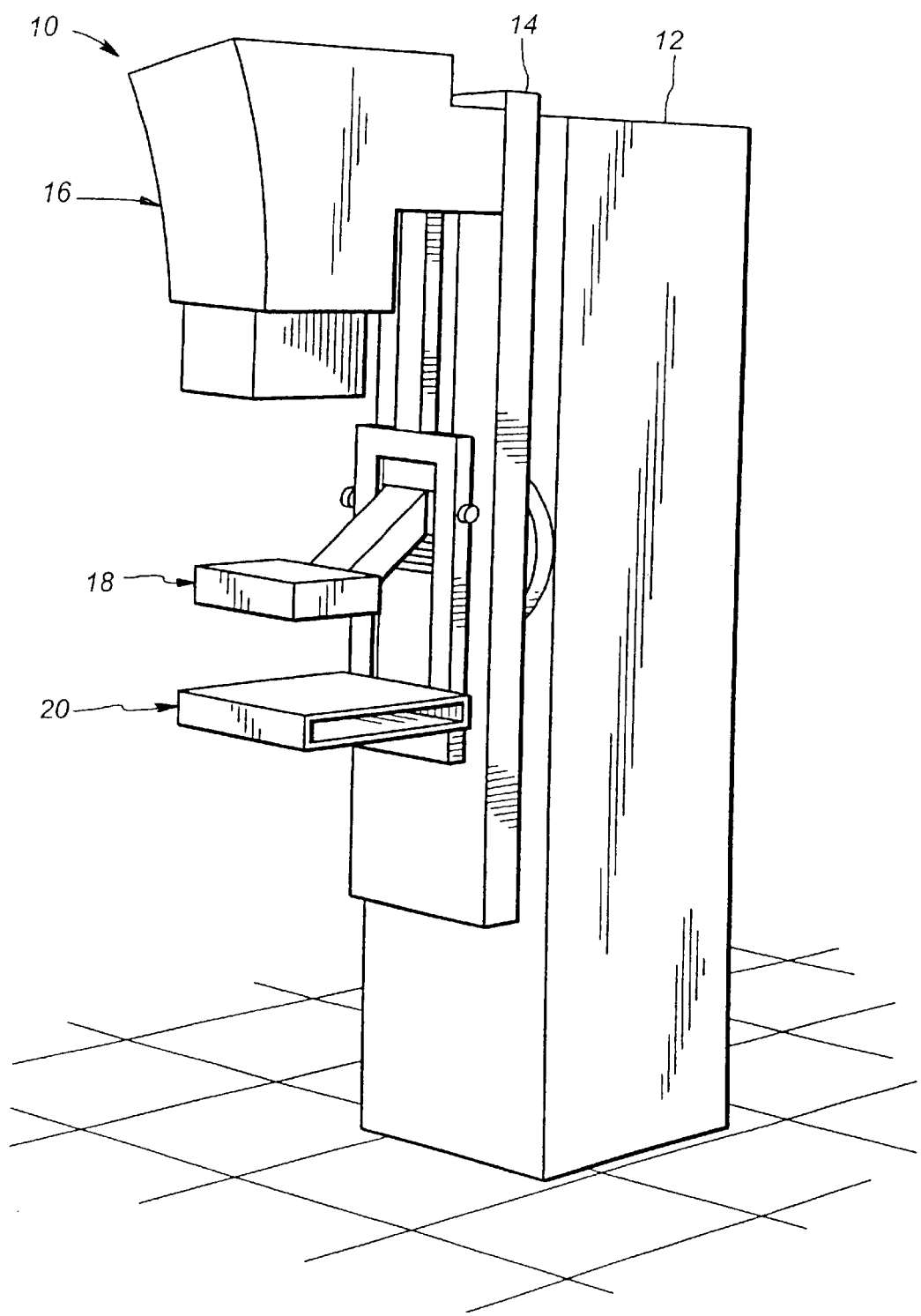
FIG. 1 is a perspective view of a mammography unit, including a compression paddle and an x-ray plate.
Figure 2A:
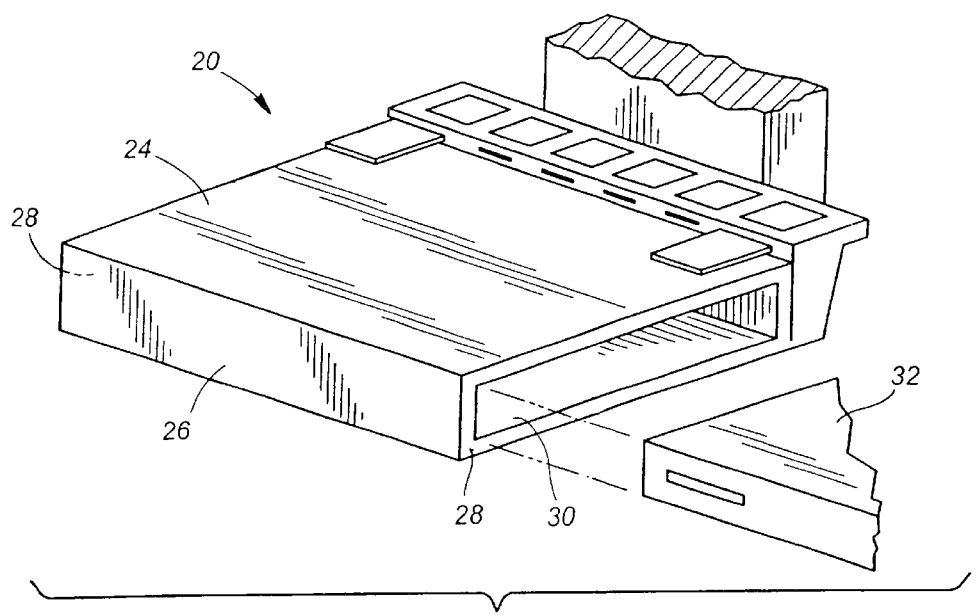
FIGS. 2A and 2B are perspective views of the x-ray plate and compression paddle, respectively, of FIG. 1.
Figure 2B:
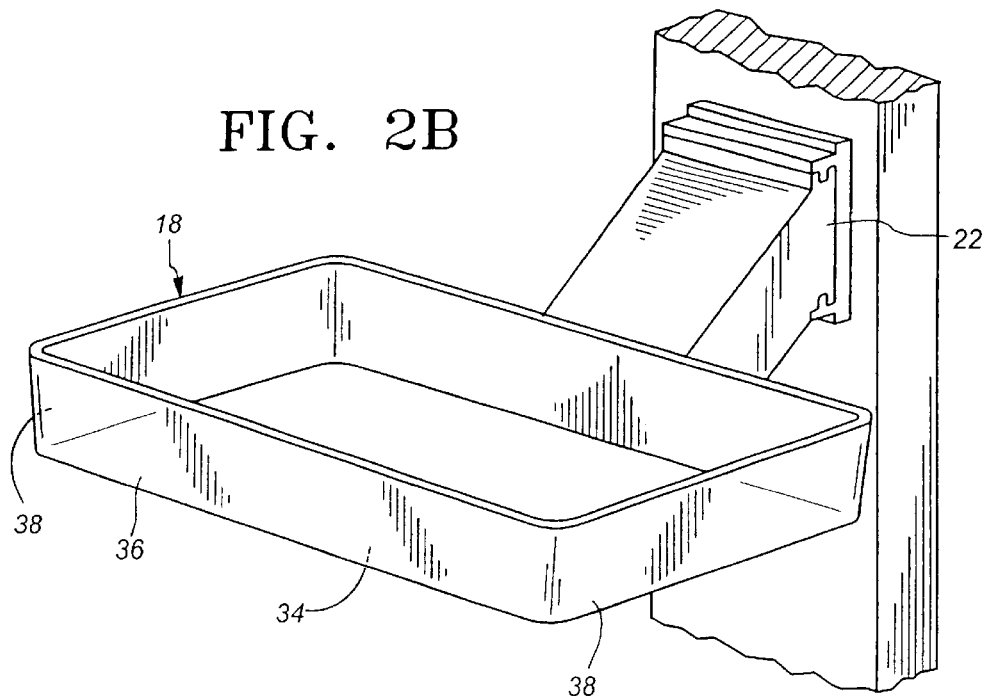
Figure 3A:
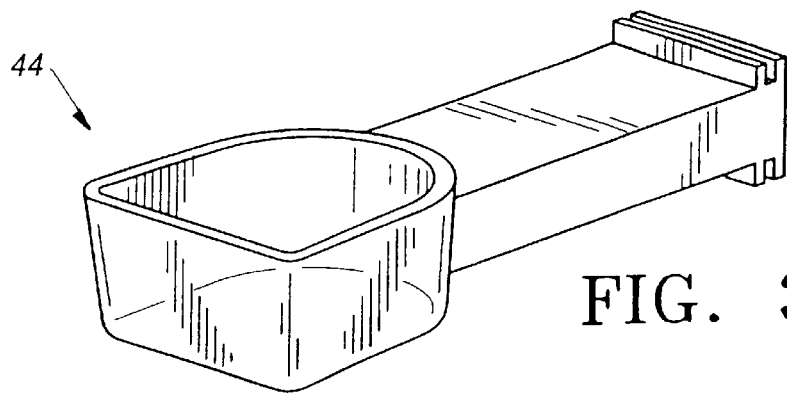
FIGS. 3A–3C are perspective views of other configurations of compression paddles that may be used with the mammography unit of FIG. 1.
Figure 3B:
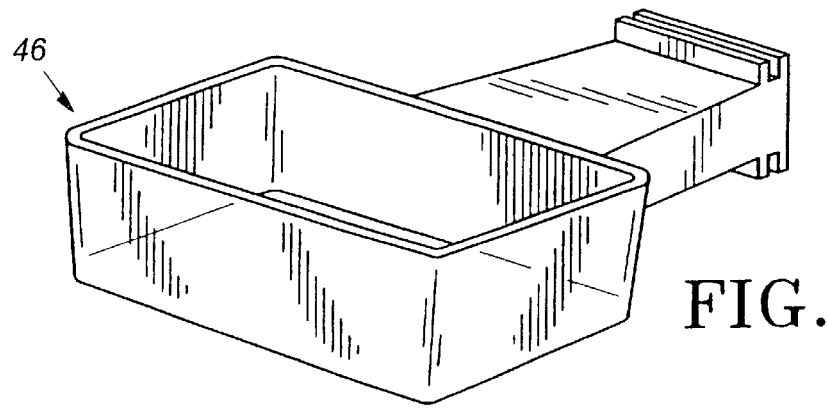
Figure 3C:
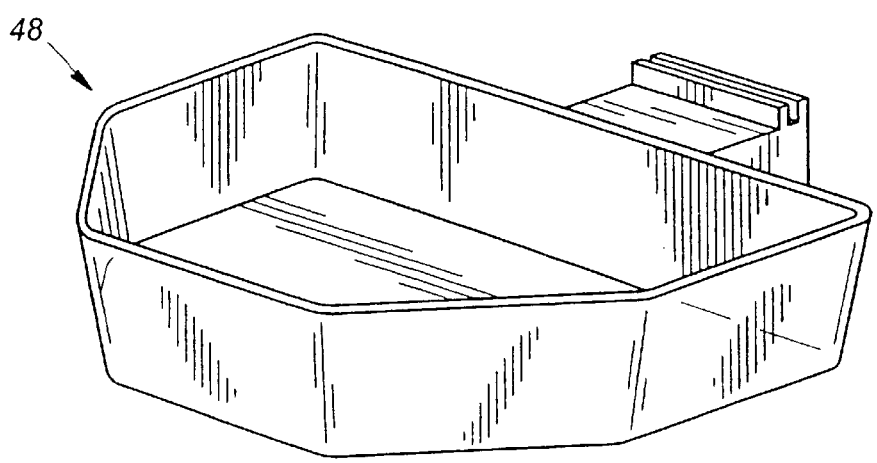
Figure 4A:
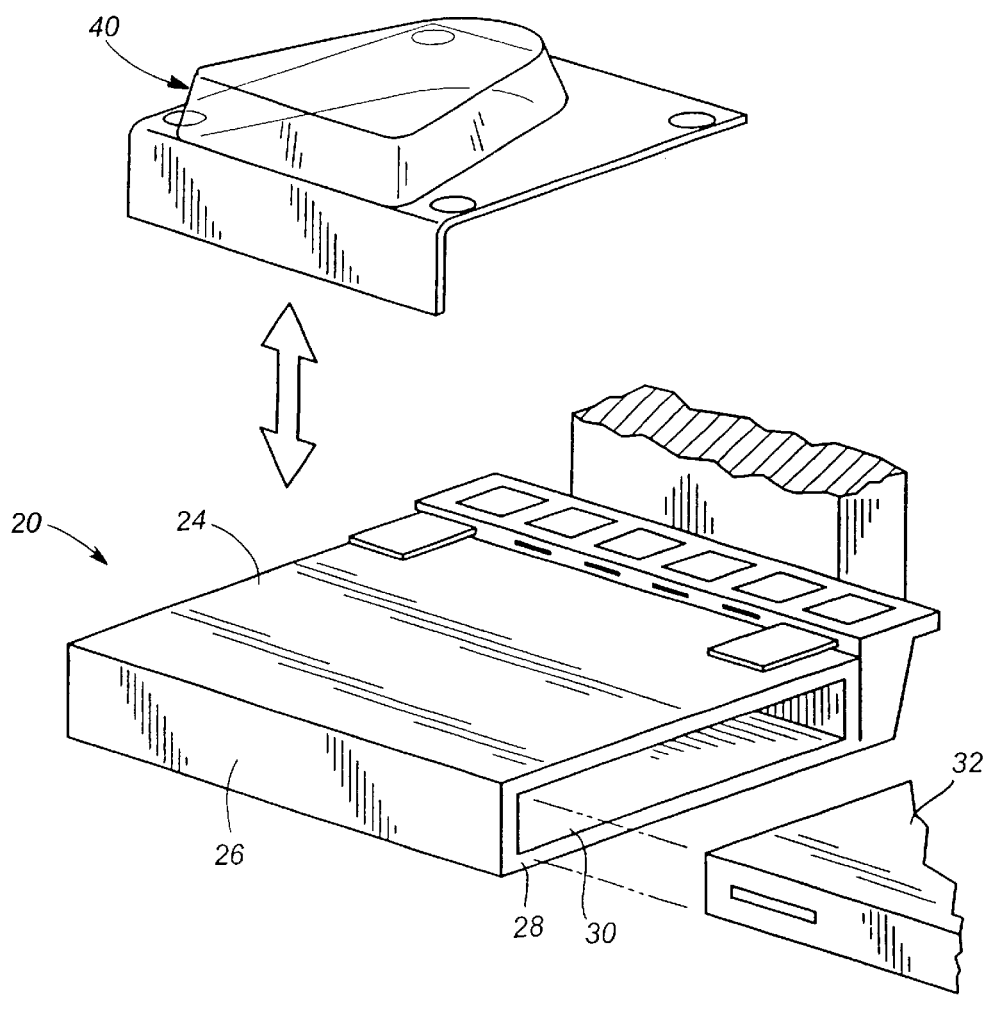
FIGS. 4A and 4B are perspective views of attachments that may be placed on the x-ray plate of the mammography unit of FIG. 1.
Figure 4B:
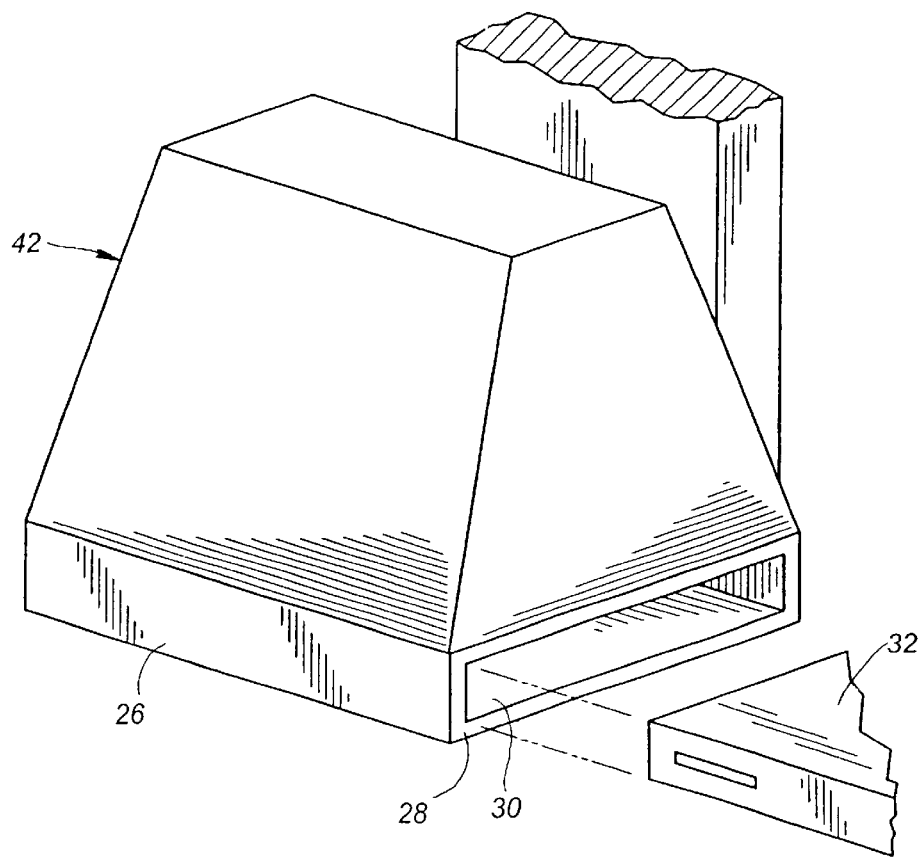

A similar pad 210, such as that shown in FIG. 7A, may be applied to an x-ray plate 20, such as that shown in FIG. 2A. When a central region 220 of the pad 210 is applied to a primary contact surface 24, a front region 228 may be applied to a front surface 26, and wings 222 (or other side regions, not shown) may cover side surfaces 28. During a mammography procedure, however, it may be necessary to access an opening 30 in one or both side surfaces 28, e.g., to insert an x-ray cassette 32 (shown in FIG. 2A). To allow such access, the wing(s) 222 may include a reusable adhesive (not shown) that may allow attachment of the wing(s) 222 to the side surface(s) 28, but allow removal without disturbing the rest of the pad 222 to allow insertion of the x-ray cassette 32. The wing 222 may then be reapplied to the side surface 28, thereby providing cushioning along the side surface 28 further during the procedure.

Figure 9:
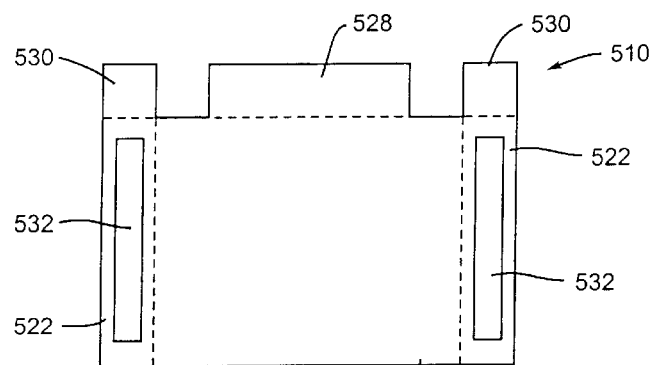
FIG. 9 is a top view of a another embodiment of a pad, including slots, in accordance with the present invention.

Preferably, turning to FIG. 9, another embodiment of a pad 510 is shown that may be used to provide cushioning along the x-ray plate 20 (not shown in FIG. 9, see FIG. 2A) while providing access to an opening 30 in a side surface 28 of the x-ray plate 20. The pad 510 generally includes a central region 520, a front region 528, and side regions 522 including ears 530, similar to the embodiment shown in FIG. 7B. In addition, one or both side regions 522 may also include a slot 532 therethrough that corresponds substantially to the shape of the opening 30 in the side surface 28 of the x-ray plate 20. When the pad 510 is applied to the x-ray plate 20, the slot(s) 532 may allow insertion and/or removal of an x-ray cassette 32 into and/or out of the opening(s) 30 in the x-ray plate 20.

Figure 7C:
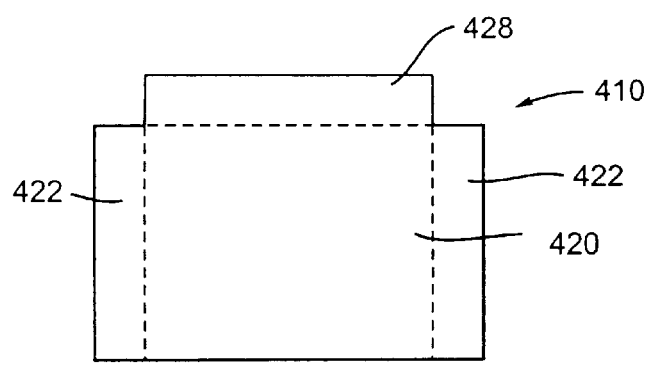

Alternatively, other pad configurations, such as those shown in FIG. 7A or 7C may be used with slots (not shown) provided in the wings 222 or side regions 422. In further alternatives, different pad segments may be removably and/or permanently attached to an x-ray plate, compression paddle, or other compression device.

Figure 10A:
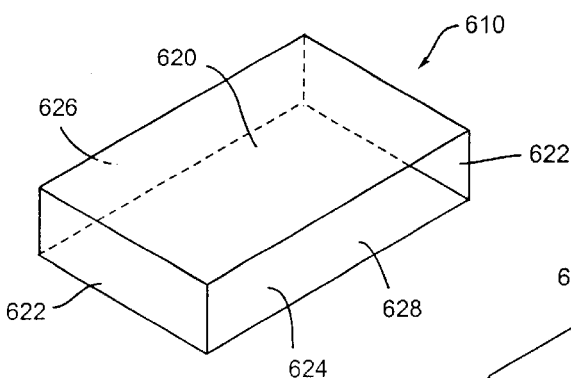
FIGS. 10A–10C are perspective views of various embodiments of slip-over pads, in accordance with the present invention.
Figure 10B:
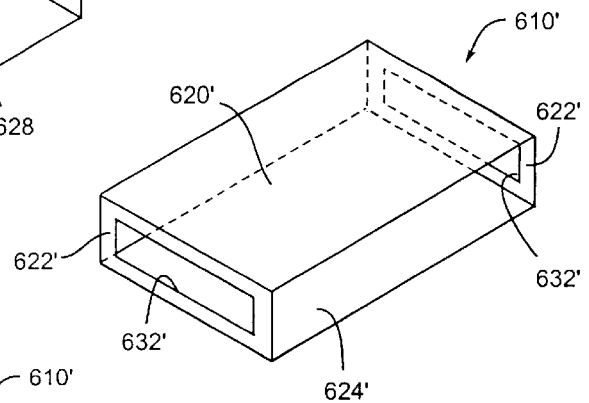
Figure 10C:
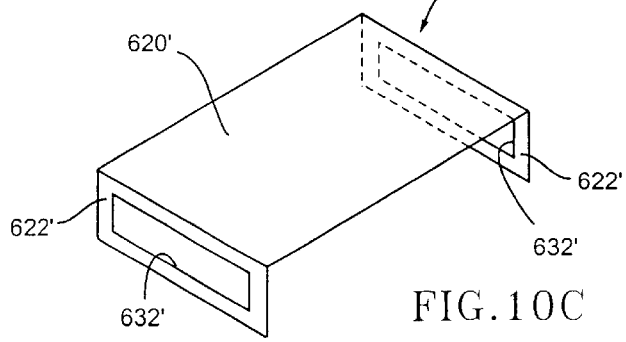

Turning to FIGS. 10A–10C, slip-over pads may be provided instead of the generally planar pads described above. The slip-over pads may be preformed to include multiple panels that may be removably secured around a compression device, such as the x-ray plate 20, shown in FIG. 2A.

In a first embodiment, shown in FIG. 10A, a five-sided slip-over pad 610 is shown that includes a top panel 620, side panels 622, and a bottom panel 624, defining an opening 628, as well as, optionally, including a back panel 626. The slip-over pad 610 may be formed from one or more sheets of material, similar to the pads described above. Preferably, the panels 620, 622, 624, 626 are formed from a single sheet of padding material that are cut and/or folded into a sleeve shape. Any seams (not shown) may be connected by beveling, lapping, and/or butting mating edges or surfaces of the sheet, and bonding them, e.g., using an adhesive, sonic welding, and the like.

Preferably, the padding material is radiolucent. Alternatively, one or more regions of one or more panels (e.g., the top and bottom panels 620, 624) may be radiolucent, while the remainder of the padding material need not be, similar to the pad shown in FIG. 12A. Any adhesive and the like that is used may also be radiolucent, e.g., if it will be exposed within the field of the x-ray plate 20.

An inside surface of the slip-over pad 610 may be substantially smooth and free of adhesive to allow the x-ray plate 20 to be slidably received in the opening 628, e.g., until the x-ray plate 20 abuts the back panel 626. The slip-over pad 610 may be sized to fit around the x-ray plate 20 without sliding substantially during a mammography procedure, e.g., due to friction between the padding material and the x-ray plate surfaces. Alternatively or in addition, one or more inside surfaces of the slip-over pad 610 may include a texture to enhance the frictional engagement with the x-ray plate 20 and/or an adhesive may be applied, similar to the embodiments described above, that allow the clip cover pad 610 to be secured yet slidably removable from the x-ray plate 20.

In an alternative embodiment, shown in FIG. 10B, a slip-over pad 610' may include one or more slots 632 corresponding to opening(s) in the x-ray plate 20 (not shown, see FIG. 2A), similar to the embodiments described above. In a further alternative, shown in FIG. 10C, a slip-over pad 610" may be provided that does not include a bottom panel. In this embodiment, the top and side panels 620", 622" (and the back panel, not shown, if included) may be sufficiently rigid relative to one another in order to fit snugly around the x-ray plate 20, either with or without using an adhesive, textured surfaces, or other altered surfaces.

Figure 11:
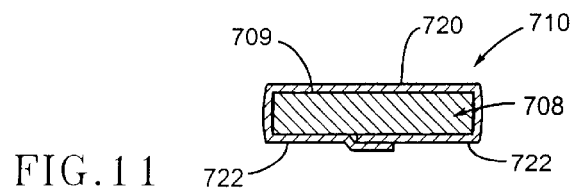
FIG. 11 is a cross-sectional view of a wrap-around pad secured around a compression device, in accordance with the present invention.

Turning to FIG. 11, a wrap-around pad 710 is shown that generally includes a central region 720 and a pair of side regions 722. The central region 720 may be aligned with a primary contact surface 709 of a compression device 708, such as an x-ray plate, while the side regions 722 extend around the compression device 708 to substantially secure the pad 710 relative to the compression device 708. The pad 710 may be constructed similarly to the pads described above, i.e., including a padding layer. For example, as shown in FIG. 12A, a pad 710 may be formed from radiolucent material.

The side regions 722 may wrap entirely around the compression device 708 until they overlap one another. The side regions 722 may include cooperating connectors, e.g., one or more layers of adhesive, hook and loop connectors, and the like, that may secure the side regions 722 together. Alternatively, a layer of adhesive (not shown) may be provided along all or a portion of the surface of the pad 710 contacting the compression device 708. For example, the side regions 722 may be sufficiently long to extend around to a lower surface of the compression device 708 without overlapping one another, but may include a layer of adhesive, a textured surface, and/or other altered surface to attach to the lower surface of the compression device 708. Although the side regions 722 are shown as being symmetrical, it will be appreciated that one may be longer than the other, e.g., if desired to move the overlap region out of the field of the x-ray plate.

Figure 12B:
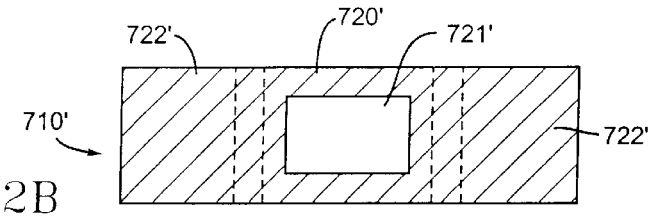
Figure 12C:
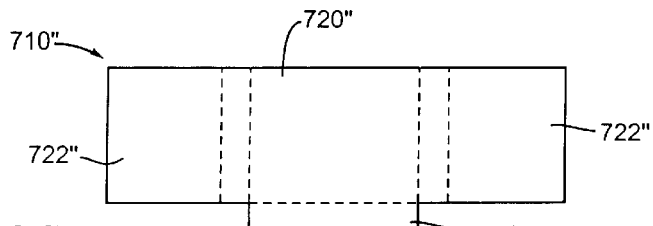

Turning to FIG. 12B, another pad 710' is shown that includes a radiolucent region 721' in the central region 720', while the remainder of the central region 720' is not necessarily radiolucent (e.g., radiopaque). The side panels 722' are shown as being radiopaque, although some regions may also be radiolucent, e.g., any regions that extend into the field of the x-ray plate. In a further alternative, shown in FIG. 12C, a pad 710", which may be entirely or only partially radiolucent, may include a front region 728" that may be bent and applied to a front surface of a compression device (not shown).

Figure 12D:
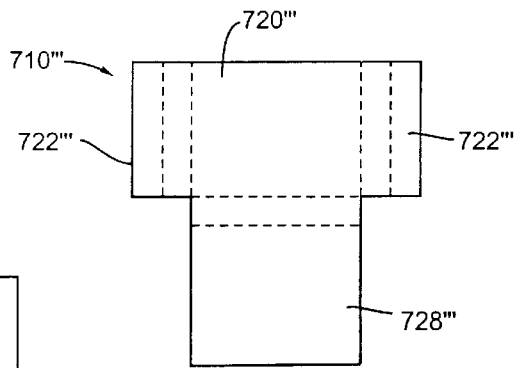

Turning to FIG. 12D, another pad 710''' is shown that includes a front region 728''' that is sufficiently long to extend to a lower surface of the compression device, whereupon the side regions 722''' may overlap and/or be secured to the front region 720''' along the lower surface. In further alternatives (not shown), any of these embodiments may include one or more slots corresponding to an opening in an x-ray plate (not shown), similar to the embodiments described above.

Figure 13A:
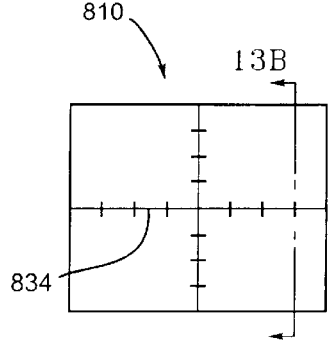
FIG. 13A is a top view of another pad including radiopaque markings, in accordance with the present invention.
Figure 13B:
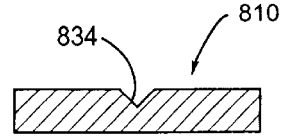
FIG. 13B is a cross-section of the pad of FIG. 13A.

Turning to FIGS. 13A and 13B, another embodiment of a pad 810 is shown that includes a central region 820 including radiolucent padding material, similar to the previous embodiments. Optionally, the pad 810 may include slots, side regions, front regions, and/or may be formed into a slip-over and/or wrap-around pad (not shown), as described above. Unlike the previous embodiments, the pad 810 includes markings formed therein, thereby providing a grid 834, as best seen in FIG. 13A.

In one embodiment, the grid 834 may be formed by cutting notches, molding indents, and the like into one or both upper and lower surfaces of the pad 810, as shown in FIG. 13B. Alternatively, notches may be provided in one or more edges (not shown) of the pad 810 to assist in aligning a tissue structure (not shown) on the pad 810. In a further alternative, the grid 834 may be printed on one or both surfaces or embedded into the padding layer (not shown), e.g., during a foaming, die cutting, or molding process used to create the padding layer, or a pad printing process. In a further alternative, the grid 834 may be manually printed onto the exposed surface of the pad 810 shortly before performing a mammography procedure. Although a grid 834 is shown, other markings (not shown) may be provided that may assist in orienting a tissue structure applied against the pad 810.

Turning to FIG. 14, another embodiment of a pad 910 is shown, in accordance with the present invention. The pad 910, which may be formed from materials and/or including an adhesive or texturing, similar to the embodiments described above, generally includes a panel 912 defining a window 932 formed therein. Preferably, as shown, the panel 912 has a "U" shape defining opposing side regions 934 on either side of the window 932. Alternatively, the panel may be rectangular or may include any of the shapes described above, yet having a window cut or otherwise formed in the panel (not shown).

The pad 910 may be secured to a primary contact surface of a compression device, e.g., on a stereotactic biopsy apparatus, e.g., a vertically mounted compression device (not shown). A tissue structure, e.g., a patient's breast, may be compressed against the pad 910 such that a target region of the tissue structure is disposed within the window, e.g., to facilitate obtaining a biopsy and the like, as is well known in the art.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An apparatus for compressing a tissue structure, comprising:
    a compression device including a primary contact surface comprising radiolucent material lying within a field of an x-ray source for obtaining an x-ray of a tissue structure disposed in the field, and one or more side surfaces extending laterally from the primary contact surface; and
    a pad comprising compressible material secured to the compression device, the pad including a tissue contact surface comprising radiolucent material removably secured against the primary contact surface of the compression device, and one or more side regions removably secured along respective side surfaces of the compression device.

2. An apparatus for compressing a tissue structure, comprising:
    a compression device including a primary contact surface comprising radiolucent material, and one or more side surfaces extending laterally from the primary contact surface; and
    a pad comprising compressible material secured to the compression device, the pad including a tissue contact surface comprising radiolucent material removably secured against the primary contact surface, and one or more side regions removably secured along respective side surfaces of the compression device,
    wherein the tissue contact surface comprises markings for orienting a tissue structure applied against the tissue contact surface.

3. The apparatus of claim 1, wherein the entire pad is formed from radiolucent material.

4. An apparatus for compressing a tissue structure, comprising:
    a compression device including a primary contact surface comprising radiolucent material, and one or more side surfaces extending laterally from the primary contact surface; and
    a pad comprising compressible material secured to the compression device, the pad including a tissue contact surface comprising radiolucent material removably secured against the primary contact surface, and one or more side regions removably secured along respective side surfaces of the compression device,
    wherein the tissue contact surface comprises a radiolucent region and a radiopaque region.

5. The apparatus of claim 1, wherein the one or more side regions comprise a pair of side regions extending from opposing edges of the tissue contact surface, the side regions extending around the compression device.

6. The apparatus of claim 5, wherein the side regions connect to one another such that the tissue contact surface is secured adjacent the primary contact surface of the compression device.

7. The apparatus of claim 5, wherein the pad comprises a front region attached to a front surface of the compression device.

8. The apparatus of claim 7, wherein the front region is sufficiently long such that the front region and at least one of the side regions overlap to substantially secure the pad to the compression device.

9. The apparatus of claim 1, wherein the pad comprises a sleeve that is slidably received around at least a portion of the compression device, the pad sized to slidably engage the compression device sufficiently to secure the tissue contact surface adjacent the primary contact surface.

10. The apparatus of claim 9, wherein the sleeve comprises a top panel and a bottom panel secured opposite one another by side panels extending therebetween.

11. An apparatus for compressing a tissue structure, comprising:
    a compression device including a primary contact surface comprising radiolucent material, and one or more side surfaces extending laterally from the primary contact surface; and
    a pad comprising compressible material secured to the compression device, the pad including a tissue contact surface comprising radiolucent material removably secured against the primary contact surface, and one or more side regions removably secured along respective side surfaces of the compression device,
    wherein the one or more side regions comprise a side region including a slot therein corresponding to an opening in a side surface of the compression device, thereby providing access to the opening when the side region is secured adjacent the side surface.

12. The apparatus of claim 1, wherein the pad is removably secured to the compression device.

13. The apparatus of claim 1, wherein the pad is secured to the compression device by an adhesive.

14. The apparatus of claim 1, wherein the pad comprises resiliently compressible material.

15. The apparatus or claim 1, wherein the pad comprises thermally insulating material.

16. A pad for cushioning a compression surface of a mammography unit, comprising:
    a pad comprising radiolucent material, the pad comprising first and second surfaces;

a radiolucent tape comprising a first surface attached to the first surface of the pad, and a second exposed surface comprising a radiolucent pressure sensitive adhesive for removably attaching the exposed surface to an object.

17. The pad of claim 16, further comprising a radiolucent adhesive between the first surfaces of the pad and the tape for attaching the tape to the pad.

18. The pad of claim 17, wherein the radiolucent adhesive comprises an acrylic adhesive having a thickness of not more than about three mils.

19. The pad of claim 16, wherein the pressure sensitive adhesive comprises an acrylic adhesive having a thickness of not more than about 1.25 mils.

20. The pad of claim 16, wherein the tape comprises at least one of a polyester film and a polyethylene film having a thickness of not more than about 0.5 mils.

21. The pad of claim 16, wherein the pad comprises open cell polyurethane foam having a thickness of not more than about 6.4 mm (0.25 inch).

22. The pad of claim 16, further comprises a cover sheet covering the exposed surface, the cover sheet being removable before attaching the exposed surface to an object.

23. The pad of claim 16, wherein the tape comprises substantially elastic material, whereby the resilient pad may be secured around corners while minimizing pockets and creases between the pad and a contact surface.

24. The pad of claim 16, wherein the pad comprises a radiolucent region and a radiopaque region.

25. The pad of claim 16, wherein the pad comprises a radiolucent central region, and a side region adjacent the central region, the side region including a slot therethrough.

26. The pad of claim 16, wherein the pad comprises a "U" shaped panel defining a window between opposing portions.

27. A device for attachment to a compression surface of a mammography unit, comprising:

a pad comprising radiolucent material, the pad comprising first and second surfaces, the pad comprising markings for orienting a tissue structure applied against the second surface; and means for attaching the first surface of the pad to the compression surface.

28. Tue device of claim 27, wherein the markings comprise notches or indents in at least one of the first and second surfaces.

29. The device of claim 27, wherein the markings comprise radiolucent markings printed on at least one of the first and second surfaces.

30. The device of claim 27, wherein the markings comprise one or more axes defined along the second surface.

31. The device of claim 27, wherein the means for attaching comprises a radiolucent adhesive applied to the first surface.

32. The device of claim 27, wherein the means for attaching comprises a texture on the first surface.

33. The device of claim 27, wherein the means for attaching comprises a tape attached to the first surface, the tape including an exposed surface comprising a pressure sensitive adhesive.

34. The device of claim 33, wherein the pressure sensitive adhesive comprises an acrylic adhesive.

35. The device of claim 33, wherein the tape comprises at least one of polyester and polyethylene.

36. The device of claim 33, wherein the tape comprises a double coated tape.

37. The device of claim 27, wherein the pad comprises resilient material.

38. The device of claim 27, wherein the pad comprises thermally insulating material.

39. An apparatus for compressing a tissue structure, comprising:

a compression device including a primary contact surface comprising radiolucent material; and a pad comprising radiolucent material removably secured against the primary contact surface, the pad comprising radiopaque markings for orienting a tissue structure applied against the pad.

40. The apparatus of claim 39, wherein the pad comprises first and second surfaces, and wherein the first surface comprises means for removably attaching the first surface of the pad to the primary contact surface.

41. The apparatus of claim 39, wherein the compression device comprises one or more side surfaces extending laterally from the primary contact surface, and wherein the pad is also removably secured to the one or more side surfaces.

42. The apparatus of claim 39, wherein the compression device comprises an opening for receiving an x-ray element therein, and wherein the pad comprises a slot therethrough corresponding to the opening.

43. The apparatus of claim 39, wherein the compression device comprises a compression panel of a stereotactic biopsy apparatus, and wherein the pad comprises a window therein.

44. The apparatus of claim 43, wherein the pad comprises a "U" shaped panel defining a window between opposing portions of the panel.

45. A compression device for a mammography unit, comprising:

a first compression plate including a primary contact surface comprising radiolucent material lying within an x-ray field of the mammography unit, and one or more side surfaces extending laterally from the primary contact surface; and a pad comprising compressible material secured to the compression plate, the pad including a tissue contact surface comprising radiolucent material adjacent the primary contact surface of the compression plate, and one or more side regions adjacent respective side surfaces of the first compression device.

46. The compression device of claim 45, wherein the pad is removably secured to the compression plate.

47. The compression device of claim 45, wherein the one or more side regions wrap at least partially around the compression plate.

48. The compression device of claim 47, wherein the one or more side regions are secured to the compression device by hook and loop connectors.

49. The compression device of claim 48, wherein the pad comprises two side regions that wrap around the compression plate and are secured to one another by the hook and eye connectors.

50. The compression device of claim 45, further comprising a second compression plate opposite the first compression plate for compressing tissue between the second compression plate and the primary contact surface of the first compression plate.

* * * * *

UNITED STATES PATENT AND TRADEMARK OFFICE
CERTIFICATE OF CORRECTION

PATENT NO. : 6,765,984 B2
DATED : July 20, 2004
INVENTOR(S) : Higgins et al.

It is certified that error appears in the above-identified patent and that said Letters Patent is hereby corrected as shown below:

Column 4,
Line 17, please change "of a another" to -- of another --
Line 26, please change "may secured " to -- may be secured --
Line 45, please change "20 alternatives" to -- alternatives --

Column 11,
Line 43, please change "28. Tue device" to -- 28. The device --

Signed and Sealed this

Nineteenth Day of October, 2004

JON W. DUDAS
*Director of the United States Patent and Trademark Office*